US010849950B2

(12) United States Patent
Nasu et al.

(10) Patent No.: US 10,849,950 B2
(45) Date of Patent: Dec. 1, 2020

(54) COMPOSITION FOR TREATING FATTY LIVER

(71) Applicant: Masanori Nasu, Shinagawa-ku (JP)

(72) Inventors: Masanori Nasu, Shinagawa-ku (JP); Da Qi Liu, Dongcheng Qu (CN)

(73) Assignee: Masanori Nasu, Shinagawa (JP)

( * ) Notice: Subject to any disclaimer, the term of this patent is extended or adjusted under 35 U.S.C. 154(b) by 0 days.

(21) Appl. No.: 16/461,144

(22) PCT Filed: Nov. 8, 2017

(86) PCT No.: PCT/JP2017/040244
§ 371 (c)(1),
(2) Date: May 15, 2019

(87) PCT Pub. No.: WO2018/092654
PCT Pub. Date: May 24, 2018

(65) Prior Publication Data
US 2020/0078429 A1  Mar. 12, 2020

(30) Foreign Application Priority Data

Nov. 18, 2016 (JP) ................................. 2016-224986

(51) Int. Cl.
A61K 36/258  (2006.01)
A61P 1/16  (2006.01)
A61K 36/076  (2006.01)
A61K 36/233  (2006.01)
A61K 36/284  (2006.01)
A61K 36/481  (2006.01)
A61K 36/708  (2006.01)
A61K 36/734  (2006.01)
A61K 36/752  (2006.01)
A61K 36/884  (2006.01)
A61P 9/00  (2006.01)
A61P 3/10  (2006.01)
A61K 36/36  (2006.01)
A61K 36/482  (2006.01)
A61K 36/488  (2006.01)
A61K 36/537  (2006.01)

(52) U.S. Cl.
CPC .......... *A61K 36/258* (2013.01); *A61K 36/076* (2013.01); *A61K 36/233* (2013.01); *A61K 36/284* (2013.01); *A61K 36/36* (2013.01); *A61K 36/481* (2013.01); *A61K 36/482* (2013.01); *A61K 36/488* (2013.01); *A61K 36/537* (2013.01); *A61K 36/708* (2013.01); *A61K 36/734* (2013.01); *A61K 36/752* (2013.01); *A61K 36/884* (2013.01); *A61P 1/16* (2018.01); *A61P 3/10* (2018.01); *A61P 9/00* (2018.01)

(58) Field of Classification Search
CPC ... A61K 36/258; A61K 36/076; A61K 36/233
See application file for complete search history.

(56) References Cited

U.S. PATENT DOCUMENTS

2016/0106793 A1   4/2016 Peltier et al.

FOREIGN PATENT DOCUMENTS

| CN | 101015668 A | | 8/2007 |
|---|---|---|---|
| CN | 101112432 A | | 1/2008 |
| CN | 100551396 C | | 10/2009 |
| CN | 101745077 A | * | 6/2010 |
| CN | 101869687 A | * | 10/2010 |
| CN | 103977112 A | * | 8/2014 |
| CN | 104857377 A | | 8/2015 |
| CN | 105250890 A | | 1/2016 |
| JP | 57-70818 A | | 5/1982 |
| JP | 1-59248 B2 | | 12/1989 |
| JP | 4205188 B2 | | 1/2009 |
| JP | 2014-76962 A | | 5/2014 |

OTHER PUBLICATIONS

Office Action dated Mar. 21, 2017, in Japanese Patent Application No. 2016-224986, filed Nov. 18, 2016 (with English translation).
International Search Report dated Dec. 5, 2017 in PCT/JP2017/040244 filed on Nov. 8, 2017.
Combined Chinese Office Action and Search Report dated Oct. 31, 2019, in Patent Application No. 201780071313.8, citing documents AO-AQ and AX therein, 12 pages (with unedited computer generated English translation and English Translation of Category of Cited Documents).
Fucang, W. et al., "Common Disease Prescription", pp. 52-54.
Extended European Search Report dated Jun. 9, 2020 in Patent Application No. 17872232.8, citing documents AA, AO, AP and AW-AX therein, 5 pages.
Yuyu Qiu, et al., "Vaccarin Attenuates High Glucose-Induced Human EA•hy926 Endothelial Cell Injury Through Inhibition of Notch Signaling" Molecular Medicine Reports, vol. 13, No. 3, XP055697783; Jan. 20, 2016, pp. 2143-2150.
Minoru Sugiura, et al., "Chronic Administration of Satsuma Mandarin Fruit (*Citrus Unshiu* Marc.) Improves Oxidative Stress in Streptozotocin-Induced Diabetic Rat Liver" Biol. Pharm. Bull., vol. 29, No. 3, XP055698510; Mar. 1, 2006, pp. 588-591.
Elizabeth Hernandez-Perez, et al., "Liver Steatosis and Nonalcoholic Steatohepatitis: from Pathogenesis to Therapy" Medwave, vol. 16 No. 8, e6535, XP055697781, Sep. 1, 2016, 22 pages.

* cited by examiner

*Primary Examiner* — Amy L Clark

(74) *Attorney, Agent, or Firm* — Oblon, McClelland, Maier & Neustadt, L.L.P.

(57) ABSTRACT

A composition for treating fatty liver which comprises extracts of *ginseng, Atractylodes* rhizome, *Crataegus* cuneate, *Alisma* tuber and *Cassia obtusifolia* L.

5 Claims, No Drawings

COMPOSITION FOR TREATING FATTY LIVER

TECHNICAL FIELD

The invention relates to a therapeutic composition for treating fatty liver prescribed based on Clinical Traditional Chinese Medicine.

BACKGROUND ART

In many cases, liver dysfunction that, it is said, one out of four Japanese suffer from, is fatty liver. Fatty liver is one of lifestyle-related diseases, and patients notice it first, in many cases, only when the fatty liver is found in a health examination or comprehensive medical examination because most cases are asymptomatic. Fatty liver may progress to cirrhosis and hepatitis when it is left untreated.

Treatment of fatty liver includes a dietary therapy, exercise therapy, pharmacological treatment and the like. Though dietary therapy and exercise therapy are important for patients with fatty liver, these therapies require the patients to change their lifestyle and therefore it is quite difficult for the patients to pursue these therapies.

Ursodeoxycholic acid (referred to as "Urso"), polyenephosphatidylcholine, diisopropylamine dichloroacetate and the like are known as therapeutic drugs for treating fatty liver in Western medicine. Urso is a hepatoprotector for chronic hepatitis and does not actually treat fatty liver. In addition, polyenephosphatidylcholine and diisopropylamine dichloroacetate are used for indirectly improving the condition of fatty liver and not for treating fatty liver itself.

In Kampo (Japan's assimilated version of Traditional Chinese Medicine (TCM)), there are known prescriptions that treat fatty liver. Frequently used prescriptions include "bofutsushosan (防風通聖散, fáng fēng tōng shèng sǎn; Divaricate Saposhnikovia Miraculous Powder)", "daisaikoto (大柴胡湯, dà chái hú tāng; Major *Bupleurum* Decoction)", and "tokakujokito (桃核承気湯, táo hé chég qì tāng; Peach Kernel Purgative Decoction)". However, these prescriptions do not have direct therapeutic effects on the fatty liver; it is said that their primary effects are general health-promotion benefits.

Furthermore, in certain cases, neither pharmacological treatment in conventional Western medicine nor Kampo medicine has significantly improved the condition of fatty liver.

SUMMARY OF INVENTION

An object of the invention is to provide a therapeutic composition (Kampo prescription) which can significantly improve the condition of fatty liver even in cases where there is no improvement by conventional dietary therapy, exercise therapy and/or pharmacological treatment.

Furthermore, an object of the invention is, by classifying fatty liver into plural types, to provide a therapeutic composition (Kampo prescription) that is more effective for treating each type of fatty liver.

According to the invention, the following therapeutic compositions for fatty liver are provided.

1. A therapeutic composition for treating fatty liver comprising the extracts of *Ginseng, Atractylodes* Rhizome, *Crataegus* Fruit, *Alisma* Tuber and *Cassia* Seed.

2. The therapeutic composition for treating fatty liver according to 1, further comprising the extracts of *Poria Sclerotium*, Rhubarb, *Citrus Unshiu* Peel, *Bupleurum* Root and *Astragalus* Root.

3. The therapeutic composition for treating fatty liver according to 2, wherein the composition is used for treating fatty liver unaccompanied by a disease other than fatty liver.

4. The therapeutic composition for treating fatty liver according to 1, further comprising the extracts of *Salvia Miltiorrhiza* Root, *Pueraria* Root, *Polygonum* Root, *Vaccaria Segetalis* and Cnidium Rhizome.

5. The therapeutic composition for treating fatty liver according to 4, wherein the composition is used for treating fatty liver accompanied by cardiovascular disorder.

6. The therapeutic composition for treating fatty liver according to 1, further comprising the extract of *Eucommia* Bark, *Lycium* Fruit, *Cistanche* Herb, *Dioscorea* Rhizome and *Cornus* Fruit.

7. The therapeutic composition for treating fatty liver according to 6, wherein the composition is used for treating fatty liver accompanied by diabetes mellitus.

According to the invention, a therapeutic composition (Kampo prescription) for treating fatty liver that can significantly improve the condition of the fatty liver can be provided.

According to the invention, fatty liver can be classified into plural types, and an effective therapeutic composition (Kampo prescription) can be provided for each type of fatty liver.

DESCRIPTION OF EMBODIMENTS

A therapeutic composition for treating fatty liver according to the invention (hereinafter, referred to as a composition of the invention) is characterized by comprising the extracts of *Ginseng, Atractylodes* Rhizome, *Crataegus* Fruit, *Alisma* Tuber and *Cassia* Seed.

In this description, the term "extract" means an extracted material.

In Western medicine, fatty livers are regarded as in one category, and often treated alike using a single uniform pharmacological treatment. However, in Kampo medicine, fatty liver is classified into five types, and medical treatment using an optimized prescription is performed for each type.

To treat fatty liver using the composition of the invention, an optimized prescription is prepared depending on the type of fatty liver, and contains at least five kinds of ingredients mentioned above.

Among patient groups with fatty liver classified into the five types, the invention mainly provides suitable prescriptions particularly for the following three types of fatty liver.

A. Standard type: A group of patients without any disease or history of any disease other than fatty liver B. Cardiovascular disorder type: A group of patients with cardiovascular disease or the history of cardiovascular disease other than fatty liver C. Diabetes mellitus type: A group of patients with diabetes mellitus other than fatty liver A therapeutic composition for treating fatty liver according to the invention to treat a standard type of fatty liver (hereinafter, referred to as a composition for a standard type of fatty liver) comprises the extracts of *Poria Sclerotium*, Rhubarb, *Citrus Unshiu* Peel, *Bupleurum* Root, and *Astragalus* Root, in addition to the five kinds of ingredients mentioned above.

A therapeutic composition for treating fatty liver according to the invention to treat a cardiovascular disorder type of fatty liver (hereinafter, referred to as a composition for a cardiovascular disorder type of fatty liver) comprises the extracts of *Salvia Miltiorrhiza* Root, *Pueraria* Root, Polygonum Root, *Vaccaria Segetalis* and Cnidium Rhizome in addition to the five kinds of ingredients mentioned above.

A therapeutic composition for treating fatty liver according to the invention to treat a diabetes mellitus type of fatty liver (hereinafter, referred to as a composition for the diabetes mellitus type of fatty liver) comprises the extracts of *Eucommia* Bark, *Lycium* Fruit, *Cistanche* Herb, *Dioscorea* Rhizome and *Cornus* Fruit in addition to the five kinds of ingredients mentioned above.

According to the composition of the invention, the improvement in liver functions was significantly recognized for patients with fatty liver for which improvement was not seen by conventional treatment.

Specifically, the increase in adiponectin level in the blood, a protein secreted by adipocytes, and the reduction of transaminase level in the blood, which is abundant in the hepatocytes, were confirmed. The details will be explained in Test examples later.

(prophylaxis and treatment of diseases by a dietary regimen) based on Clinical Traditional Chinese Medicine.

Also, Masanori Nasu, another inventor of the invention, is an expert in procuring, processing, obtaining extracts, and performing the quality control of Kampo crude drugs. Nasu achieved to produce the compositions of the invention by using Kampo prescriptions formulated by Liu and optimizing them as extracts to be administered to patients.

The name of each Kampo crude drug used in the scope of patent claims of the application is based on the gloss index of "Kampo Igaku Daijiten 1 Yakubutsu-hen (Kampo Medicine Dictionary 1 pharmacological drug section)" (Edited by People's Medical Publishing House Co. Ltd., published by Yukonsha Co. Ltd.). As can be seen from the following description, the same Kampo crude drug may have plural another names. Therefore, even if a Kampo crude drug used in the invention is written in another name, the Kampo crude drug is the same as the Kampo crude drug used in the invention. The Table shown below summarizes the names of Kampo crude drugs used in the scope of patent claims and another name of them.

TABLE 1

| Name of Kampo crude drug (Chinese character) | Another name |
|---|---|
| 人参 Ginseng | 人俺 rén xián、神草 shén cǎo、棒槌 bàng chuí |
| 白朮 Atractylodes Rhizome | 白術 báishù、於朮 yú shù、冬朮 dōng shù、山薊 shān jì、山精 shān jīng |
| 山楂 Cragaegus Fruit | 棠梂子 táng qiú zi、紅果子 hóng guǒzi |
| 沢瀉 Alisma Tuber | 澤瀉 zé xiè、水瀉 shuǐ xiè、及瀉 jí xiè、芒芋 máng yù、天秃 tiān tū |
| 決明子 Cassia Seed | 草決明 cǎo jué míng、馬蹄決明 mǎtí jué míng、假緑豆 Jiǎ lǜdòu |
| 茯苓 Portia Sclerotium | 伏兎 fú tú、白茯苓 bái fúlíng、雲苓 yún líng |
| 大黄 Rhubarb | 将軍 jiāngjūn、川軍 chuānjūn、錦紋大黄 jǐn wén dàhuáng |
| 橘皮 Citrus Unshiu Peel | 陳皮 chénpí、紅皮 hóng pí、黄橘皮 huáng jú pí |
| 柴胡 Bupleurum Root | 北柴胡 běi chái hú、津柴胡 jīn chái hú、植柴胡 zhí chái hú |
| 黄耆 Astragalus Root | 黄耆 huáng qí、綿黄耆 mián huáng qí、箭芪 jiàn qí |
| 丹参 Salvia Miltiorrhiza Root | 紅根 hónggēn、紫丹参 zǐ dānshēn、血参根 xuè cān gēn、大紅袍 dàhóng páo |
| 葛根 Pueraria Root | 甘葛 gān gé、粉葛 fěn gé |
| 何首烏 Polygonum Root | 首烏 shǒu wū、地精 dìjīng、紅内消 hóng nèi xiāo、赤首烏 chi shǒu wū、小独根 xiǎo dú gēn |
| 王不留行 Vaccaria Segetalis | 留行子 liú hàng zi、全不留 quán bù liú、麦藍子 mài lánzi、大麦牛 dàmài niú、奶米 nǎi mǐ、王捋牛 wáng mǔ niú |
| 川芎 Cnidium Rhizome | 芎藭 qiōng qióng、撫芎 fǔ qiōng |
| 杜仲 Eucommia Bark | 木綿 mùmián、思仲 sī zhòng、糸棉皮 mì mián pí、扯糸皮 chě mì pí、糸連皮 sī lián pí |
| 枸杞子 Lycium Fruit | 杞子 qǐ zi、枸杞果 gǒuqǐ guǒ |
| 肉蓯蓉 Cistanche Herb | 地精 dìjīng、大芸 dà yún、金笋 jīn sǔn、寸芸 cùn yún |
| 山薬 Dioscorea Rhizome | 山薯 shān shǔ、懐山薬 huáishān yào |
| 山茱萸 Cornus Fruit | 山萸肉 shān yú ròu、肉棗 ròu zǎo、薬棗 yào zǎo |

The compositions of the invention contain various kinds of Kampo crude drugs, and a therapeutic effect for treating fatty liver can be obtained by the synergetic effect of these multiple ingredients. The inventors of the invention formulated the compositions of the invention, namely the combination of Kampo crude drugs, based on their knowledge and experience on Kampo medicine.

Liu Da Qi, one of the inventors of the invention, devised a Kampo prescription of the invention. Currently, Liu is a leading Chinese scholar in the world's only established operation of a custom-made medicine system by Rokushin/Juchi therapy (composed of six diagnoses and ten treatments) and the classic nutrition study, that is, dietary therapy Hereinafter, Kampo crude drugs used for the composition of the invention will be explained individually on their original plant source, main ingredient, place of harvest, taste and nature, efficacy, effect, clinical application and the like. Efficacy effect and clinical application are described for each crude drug alone. The efficacy and the like are not for combination of crude drugs.

1. Commonly Used Ingredients

*Ginseng:*

Original plant source: The root of *Panax ginseng* in the family Araliaceae

Ingredients: More than 13 types of panaxosides (it is also called as ginsenoside), Main ingredient is saponin.

Place of harvest: Jilin, Liaoning and the like

Nature (xìng or qì) and taste: Sweet, slightly bitter, warm. Qì enters the spleen/lung meridians.

Efficacy: To fortify the deficit of qì and stabilize a prostration state, fortify the lung functions and replenish the spleen. Seishin (生津, shēng jīn; to promote the excretion of saliva or body fluid), Anshin (安神, ān shén; to relieve uneasiness of mind and body tranquilization), Yakuchi (益智, yì zhì; to activate the cerebral functions)

Effect: It is able to enhance nonspecific resistance (immune response) of the human body, and modify the predisposition to the onset of diseases, and can restore aberrant conditions to a normal state of health.

*Ginseng* used for the composition of the invention is preferably Chinese *ginseng* (*Panax ginseng* C. A. Mey.) (referred to as Korean *ginseng* or Goryeo *ginseng*) and Kojin (red *ginseng*) that are thought to have high efficacy.

*Atractylodes* Rhizome:

Original plant source: Root of *Atractylodes ovata* DC. in the family Compositae Ingredients: Main ingredients are atractylol, atractylon and the like Place of harvest: Zhejiang, Anhui and the like Nature (xìng or qì) and taste: Sweet, bitter, warm. Qì enters the spleen/stomach meridians.

Efficacy: Kenpi (健脾, jàn pí; to fortify the spleen), Ekki (益气, yì qì; to replenish qì), Soshitu (燥湿, zào shī; to relieve dampness from the body), Shotan (消痰, xiāo tán; to disperse phlegm), Risui (利水, lì shuǐ; to regulate water metabolism in the body), Shikan (止汗, zhǐ hàn; to suppress sweating)

Clinical applications: Treatment for Hii Kyojaku (脾胃虚弱, pí wèi xū ruò; weak spleen and stomach), Shokusho Kentai (食少倦怠, shí xiǎo juàn dài; small appetite and fatigue), dyspepsia, Kyocho (虚張, xū zhāng; distension), Sessha (泄瀉, xiè xiè; diarrhea), Tan'in (痰飲, tán yǐn; general term of phlegm and fluid. abnormal fluids stagnated in the body), Gen un (眩暈, xuàn yūn; dizziness), Suishu (水腫, shuǐ zhǒng; edema), Odan (黄疸, huáng dǎn; jaundice), Shitsuhi (湿痺, shī bì; arthritis with fixed pain caused by dampness), Shoben Furi (小便不利, xiǎo biàn bù lì; to decrease in urinary volume, oliguria), Jikan (自汗, zì hàn; excessive perspiration) and Taido Fuan (胎動不安, tāi dòng bù ān; threatened miscarriage).

*Crataegus* Fruit:

Original plant source: Fruit of *Crataegus pinnatifida* Bge. or *Crataegus cuneate* Sieb. et Zucc. in the family Rosaceae Ingredients: The fruits of *Crataegus pinnatifida* contain crategolic acid, tartaric acid, citric acid, malic acid, flavonoid, lactone, glucoside, vitamin C, tannin, bioquercetin, and the like. The fruits of *Crataegus cuneate* contain crategolic acid, citric acid, malic acid, tannin, saponin, vitamin C, and the like.

Place of harvest: Shandong, Hebei, Henan, Jiangsu and the like

Nature (xìng or qì) and taste: Sour/sweet, lukewarm. Qì enters the spleen/stomach/liver meridians.

Efficacy: Shoshoku Kaseki (消食化積, xiāo shí huà jī; to relieve gastrointestinal undigested substances and promote digestion), San o (散瘀, sǎn yū; to improve the blood stasis). It helps digestion by increasing digestive enzymes in the gastric juice, and slightly decreases the fat levels in the blood.

Clinical applications: Treatment for Nikuseki Shokutai (肉積食滞, ròu jī shí zhì; symptoms that food and drink stagnate due to overeating meats, such as heavy stomach, loss of appetite, odorous eructation, nausea), Fukutu Sessha (腹痛泄瀉, fù tòng xiè xiè; diarrhea with abdominal pain), bacillary dysentery, Tan'in Himan Donsan (痰飲痞満吞酸, tán yǐn pǐ mǎn tūn suān; food and drink don't go down to the stomach smoothly, discomfort and distension, acid regurgitation), Odan, and Senki Hentsui Chotsu (疝気偏墜脹痛, shàn qì piān zhuì zhàng tòng; hernia/testis swelling and pain); and Treatment of hyperlipemia.

*Alisma* Tuber:

Original plant source: Groundnut of *Alisma orientalis* (Sam.) Juzep. in the family Alismataceae Ingredients: Triterpenoids such as alisol and acetate ester thereof and the like, essential oil, alkaloids, resin, asparagine, and the like Place of harvest: Fujian, Sichuan, Jiangxi Nature (xìng or qì) and taste: Sweet, cold. Qì enters the kidney/bladder meridians.

Efficacy: Risui, Sanshitsu (滲湿, shèn shī; removal of the body fluid), Setsunetsu (泄熱, xiè rè; purge heat), diuresis, anti-fatty liver Clinical applications: Treatment for Shoben Furi, Suishu Choman (水腫脹満, shuǐ zhǒng zhàng mǎn; edema and bloating with excess of body fluid), beriberi, diarrhea, Tan'in, Gen un, gonorrhea, hematuria, and leukorrhea.

*Cassia* Seed:

Original plant source: Seeds of *Cassia obtusifolia* L. or *Cassia tora* L. in the family Leguminosae Ingredients: Anthraquinones such as chrysophanol, emodin-6-methyl ether, obtusifolin, obtusin, aurantio-obtusin, chrysoobtusin, chrysophanic acid-9-anthrone and the like, and carotene Place of harvest: Anhui, Jiangsu, Zhejiang, Guangxi, Guangdong, Sichuan, and the like Nature (xìng or qì) and taste: Bitter, cool. Qì enters the liver/kidney meridians.

Efficacy: Seikan Meimoku (清肝明目, gīng gān míng mù; to clear the liver-heat and restore the function of the eyes), Juncho Tsuben (潤腸通便, rùn cháng tōng biàn; to moisten intestine and stimulate bowel movements to excrete waste products)

Clinical applications: Treatment for Mokuseki Shutsu (目赤腫痛, mù chì zhǎng tòng; congestion of the eyes with swelling and pain), Shumei Tarui (羞明多涙, xiū míng duō lèi; tears responding to the bright light (epiphora)), Seimo Naisho (青盲內障, qīng máng nèi zhàng; glaucoma and cataract), Kakumaku Kaiyo (角膜潰瘍, jiǎo mó kuì yáng; corneal ulcer), cephalalgia attributed to hypertension, Gen un, hepatitis, and habitual constipation.

2. Additional Ingredients Corresponding to the Type of Fatty Liver

A. Additional Kampo Crude Drugs for the Standard Type

*Poria* Sclerotium:

Original plant source: Dried sclerotium of *Poria cocos* (Schw.) Wolf in the family Polyporaceae Place of harvest: Anhui, Hubei, Henan, Yunnan Ingredients: Triterpene ingredients such as tumulosic acid, pachymic acid, and eburicoic acid, dehydroeburicoic acid, pnicoline acid and the like, β-pachyman, ergosterol, lecithin and the like Nature (xìng or qì) and taste: Sweet/light, flat (neutral). Qì enters the heart/spleen/kidney meridians.

Efficacy: Risui Sanshitsu (利水渗湿, lì shuǐ shèn shī; to relieve excessive water from the body), Kenpi Wai (健脾和胃, jiàn pí hé wèi; to solve the stomach problem using the drug for spleen), Neishin Anshin (宁心安神, níng xīn ān shén; to ease anxious thought and stabilize psychological conditions).

Clinical applications: Treatment for Shoben Furi, Suishu Choman, Tan'in Gaiso (痰饮咳嗽, tán yǐn ké sòu; cough due to abnormal fluids stagnated in the body), Shokusho Kanmon (食少脘闷, shí guǎn mèn; lost appetite and abdominal discomfort), diarrhea, dizziness, pulsation, and insomnia.

Rhubarb:

Original plant source: Roots or rhizome of *Rheum palmatum* L., *Rheum officinale* Baill., or *Rheum tangticum* Maxim. et Regel in the family Polygonaceae Ingredients: Anthraquinone derivatives such as Sennosides A-F, aloe-emodin, rhein, chrysophanol and the like. Others; phenolic torachrysone, catechol such as catechol tannin, and the like Place of harvest: Gansu, Qinghai, Sichuan Nature (xìng or qì) and taste: Bitter, cold. Qì enters the stomach/large intestine/liver meridians.

Efficacy: Shanetsudoku (泻热毒, xiè rè dú; to regulate excessive heat and fever), Tosekitai (荡积滞, dàng jī zhì; to eliminate waste materials accumulated in the body), Gyo Oketsu (行瘀血, xíng yū xuè; to relieve congestion and hematogenous disorder)

Clinical applications: Treatment for Jitsunetsu Benpi (实热便秘, shí rè biàn mí; moisture (body fluid) in the body will be consumed by heat, the inside of the intestines will dry and moisture will cease, so the feces will solidify), Sengo Hakkyo (谵语发狂, zhān yǔ fā kuáng; making delirious sounds, derangement), Shokushaku Teitai (食积停滞, shí jī tíng zhì; indigestion and stagnation), Fukutsu Shari (腹痛泻痢, fù tòng xiè lì; abdominal pain and diarrhea), Shitunetsu Odan (湿热黄疸, shī rè huáng dǎn; jaundice due to dampness and fever), Rindaku (淋浊, lín zhuó; dysuria and turbid urine), Soseki (溲赤, sōu chì; hematuria), Yoshu Soyo (痈肿疮疡, yōng zhǒng chuāng yáng; blotch and swelling), Bogan Sekitsu (暴眼赤痛, baò yǎn chì tòng; congested swollen eye with pain); and Treatment for hematemesis, epistaxis, Ketsuo Heikei (血瘀闭经, xuè yū bì jīng; menopause due to blood stasis), Choka (癥瘕, zhēng jiǎ; abdominal mass).

*Citrus Unshiu* Peel:

Original plant source: Ripe peel of *Citrus reticulata Blanco* in the family Rutaceae or its variants Ingredients: Limonene, hesperidin, neo-hesperidin, tangeretin, citromitin, 5-norcitromitin Place of harvest: Sichuan, Zhejiang, Fujian, and the like Nature (xìng or qì) and taste: Acrid/bitter, warm. Qì enters the spleen/lung meridians.

Efficacy: Riki (理气, lǐ qì; to tonify qì and restore the functions of qì), Kenpi, Soshitsu, Ketan (化痰, huà tán; to relieve phlegm).

Clinical applications: Treatment for Hii Kitai (脾胃气滞, pí wèi qì zhì; qì stagnation in the spleen and stomach), Kanpuku Choman (脘腹胀满, guǎn fù zhàng mǎn; abdominal fullness and distention), dyspepsia, vomiting, and hiccup; and Treatment for shisutan Yotai (湿痰壅滞, shī tán yōng zhì; stagnation or clogging of phlegm), Kyokaku Manmon (胸膈满闷, xiōng gé mǎn mèn; discomfort and distention in the chest area and diaphragm), Gaiso Tatan (咳嗽多痰, ké sòu duō tán; cough with copious phlegm).

*Bupleurum* Root:

Original plant source: Roots of *Bupleurum chinense* DC. (Manshumishimasaiko/Hirohamishimasaiko) or *Bupleurum scorzonerifolium* Willd. and the like in the family Umbelliferae Ingredients: The roots of *Bupleurum chinense* contain saikosaponins A/C/D, rutin, adonitol, α-spinasterol, essential oil and the like. The roots of *Bupleurum scorzonerifolium* Willd. contain saponin, adonitol, α-spinasterol, essential oil and the like.

Place of harvest: Liaoning, Gansu, Hebei, Henan, Hubei, Jiangsu, Sichuan and the like Nature (xìng or qì) and taste: Bitter, slight cold. Qì enters the liver/gallbladder meridians.

Efficacy: Wakai Hyori (和解表里, hé jiě biǎo lǐ; harmonize the exterior and interior), Sokan (疏肝, shū gān; soothing the liver), Shoyo (升阳, shēng yáng; invigorating the vital function of spleen).

Clinical applications: Treatment for upper respiratory infections, malaria, fevers and chills, Kyoman Kyotsu (胸满胁痛, xiōng mǎn xié tòng; chest stuffiness and hypochondriac pain), hepatitis, biliary tract infections, cholecystitis, irregular menstruation, uterine prolapse, and anal prolapse.

*Astragalus* Root:

Original plant source: Roots of *Astragalus membranaceus* (Fisch.) Bge. or *Astragalus mongholicus* Bge. in the family Leguminosae.

Ingredients: Choline, glycinebetaine, coumarin, flavonoid compounds, saponin, amino acid, trace amount of folic acid, and the like Place of harvest: Gansu, Inner Mongolia and regions of Northeast China Nature (xìng or qì) and taste: Sweet, lukewarm. Qì enters the spleen/lung meridians.

Efficacy: Hochu Ekki (补中益气, bǔ zhōng yì qì; to tonify the functions of the spleen and stomach using the drug for spleen), Kohyo (固表, gù biǎo; to consolidate the superficial resistance), Risui, Takunodoku (托脓毒, tuō nóng dú; to promote discharge of pus and toxin), Seiki (生肌, shēng jī; to promote regeneration of tissue)

Clinical applications: Treatment for Hii Kyojaku, inappetency, weariness, Kikyo Ketsudatsu (气虚血脱, xū xuè tuō; deficiency of qì (vital energy) and vibrancy, and losing blood), Horo (崩漏, bēng lòu; uterine bleeding; metrorrhagia and metrostaxis), leukorrhea, chronic diarrhea, anal prolapse, uterine prolapse, gastroptosis, and nephroptosis; Apply for Hyokyo Jikan (表虚自汗, biǎo xū zì hàn; spontaneous sweating due to exterior deficiency), Tokan (盗汗, daò hàn; night sweat); Treatment for Kikyo Suishu (气虚水肿, qì xū shuǐ zhǒng; edema due to deficiency of qì (vital energy)), and chronic nephritis; Treatment for Yoso (痈疽, yōng jū; malignant skin boil), that does not erupt for a long time, or not heal for a long time after crushed; and Treatment for peptic ulcer.

B. Additional Kampo Crude Drugs for the Cardiovascular Disorder Type

*Salvia Miltiorrhiza* Root:

Original plant source: Roots of *Salvia miltiorrhiza* Bge. in the family Labiatae Ingredients: Tanshinone I/IA/B, cryptotanshinone, hydroxytanshinone IIA, dihydrotanshinone, metacutanshinonate, miltirone, danshexinkum AB/C, β-sitosterol, 3,4-dihydroxybenzaldehyde, catechin, rutin, vitamin E and the like Place of harvest: Hebei, Anhui, Jiangsu, Sichuan and the like Nature (xìng or qì) and taste: Bitter, cool. Qì enters the heart/liver meridians.

Efficacy: Kakketsu Kyoo (活血祛瘀, huó xuè qū yū; to tonify the blood circulation and relieve congestion), Anshin Neishin (安神寧心, ān shén nìng xīn; to stabilize unstable psychological state)

Clinical applications: Treatment for irregular menstruation, menopause, Sango Otai fukutsu (産後瘀滞腹痛, chǎn hòu yū zhì fù tòng; postpartum poor blood circulation and abdominal pain), coronary heart disease, angina pectoris, Choka Shakuju (癥瘕積聚, zhēng jiǎ jī; mass in abdominal area (tumor)), Fusitsu Hitsu (風湿脾痛, fēngshī pí tòng; diseases affected on muscles or joints such as rheumatoid arthritis etc. and splenalgia), palpitation, and insomnia.

Root:

Original plant source: Roots of *Pueraria lobata* (Willd.) Ohwi in the family Leguminosae Ingredients: It contains flavones such as puerarin, puerarin xyloside, daidzein, daidzin and the like, as well as β-sitosterol, arachidonic acid and the like Place of harvest: Henan, Hunan, Zhejiang, Sichuan Nature (xìng or qì) and taste: Sweet/acrid, flat (neutral). Qì enters the spleen/stomach meridians.

Efficacy: Geki Tainetsu (解肌退熱, jiě jī tuìrè; to relieve muscles to expel heat), Toshin (透疹, tòu zhěn; to promote eruption), Seishin, Shisha (止瀉, zhǐ xiè; to stop diarrhea)

Clinical applications: Treatment for Kanbo Hatsunetsu (感冒発熱, gǎn mào fā rè; cold and onset of fever), Totsu Kokyo (頭痛項強, tóu tòng xiàng qiáng; headache, muscle stiffness in the back neck with symptoms of difficulty of moving the neck), Machin Tohatsu Fucho (麻疹透発不暢, má zhěn tòu fā bù chàng; treatment used for malfunction due to measles in the early phase), Netsubyo Hankatsu (熱病煩渇, rè bìng fán kě; febrile illness with thirst), Sessha (泄瀉, xiè xiè; diarrhea), dysentery; and Treatment for Keiko Kyotsu (頸項痛, jǐng xiàng qiáng tòng; neck pain) and angina pectoris that are attributed to hypertension.

*Polygonum* Root:

Original plant source: Groundnut root of *Polygonum multiflorum* Thunb. in the family Polygonaceae Ingredients: Chrysophanol, emodin, rhein, physcion, chrysophanic acid anthrone, lecithin and the like Place of harvest: Henan, Hubei, Guizhou, Sichuan, Jiangsu, Guangxi and the like Nature (xìng or qì) and taste: Bitter/sweet, astringent, lukewarm. Qì enters the liver/kidney meridians.

Efficacy: Hokan Ekijin (補肝益腎, bǔ gān yì shèn; to tonify liver and kidney), Yoketsu Jusei (養血渋精, yǎng xuè sè jīng; to nourish the blood and arrest seminal emission); Treatment for Kekkyo (血虚, xuèxū; blood deficiency), dizziness, tinnitus, agrypnia, Shuhatsu Sohaku (鬚髪早白, xū fà zǎo bái; gray hair in young age), Yoshitsu Nanjaku (腰膝軟弱, yāo xī ruǎn ruò; weak waist and knee), Shitai Mahi (肢体麻痺, zhī tǐ má bì; paralysis of four extremities), Kansetsu Santsu (関節酸痛, guān jié suān tòng; pain of joints), Musei (夢精, mèng jīng; wet dream), Kassei (滑精, huá jīng; spermatorrhoea), Horo, leukorrhea, Kyuri (久痢, jiǔ lì; lingering dysentery), hypertension, chronic hepatitis, Hifu Soyo (皮膚掻痒, pí fū sāo yǎng; pruritus in skin), Juncho Tsuben, detoxification, Daigyaku (戴瘧, dài nuè; ague, malaria), Choso benpi (腸燥便秘, cháng zào biàn mì; constipation due to intestinal dryness), Ruireki (瘰癧, luǒ lì; scrofula, struma), Kyugyaku (久瘧, jiǔ nuè; chronic malaria).

*Vaccaria Segetalis*

Original plant source: Seeds of *Vaccaria segetalis* (Neck.) Garcke in the family Catyophyllaceae Ingredients: vacsegoside, vaccarin and the like Place of harvest: Hebei, Shandong, Liaoning Nature (xìng or qì) and taste: Bitter, flat (neutral). Qì enters the liver/stomach meridians.

Efficacy: Gyoketsu Tsukei (行血通経, xíng xuè tōng jīng; to improve the blood circulation and induce or increase menstruation), Kanyu Shoshu (下乳消腫, xiàrǔ xiāo zhǒng; to detumescence by lactogenesis)

Clinical applications: Treatment for menopause, Nyuju Futsu (乳汁不通, rǔ zhī bù tōng; galactostasis), mastitis, orchitis, Yoshu Choso (癰腫疔瘡, yōng zhǒng dīng chuāng; furunculosis; deep-rooted boil, malignant boil).

Cnidium Rhizome:

Original plant source: Rhizome of *Ligusticum chuanxiong* Hort in the family Umbelliferae Ingredients: Essential oil, alkaloids, butylphthalide, sedanonic acid lactone, ferulic acid, phenylacetic acid methacrylate and the like Place of harvest: Sichuan Nature (xìng or qì) and taste: Acrid, warm. Qì enters the liver/liver/pericardium meridians.

Efficacy: Kakketsu Gyoki (活血行気, huóxuè xíng qì; to improve the circulation of blood and qì (vital energy)), Sanfu shisu (散風止痛, sǎn fēng zhǐ tòng; to improve heat (hot/cold) and moisture (damp/dry), and release the pain)

Clinical applications: Treatment for irregular menstruation, Sango Otai Fukutsu, Tsukei (痛経, tòng jīng; algomenorrhea), menopause, Kyokyo Chotsu (胸脇脹痛, xiōng xié zhàng tòng; distension and pain in the chest area), coronary heart disease, angina pectoris; and Treatment for Kanbo Fukan (感冒風寒, gǎn mào fēng hán; cold with chill), Hensei Zutsu (偏正頭痛, piān zhèng tóu tòng; migraine and general headache), Fukan Hitu (風寒痺痛, fēng hán bì tòng; pain or numbness of joints and muscles by cold), Yoso Soyo (癰疽瘡瘍, yōng jū chuāng yáng; swelling and ulcer on the body surface), and bruise.

C. Additional Kampo Crude Drugs for the Diabetes Mellitus Type

*Eucommia* Bark

Original plant source: Bark of *Eucommia ulmoides* Oliv. in the family Eucommiaceae Ingredients: Gutta-percha, pinoresinol diglucoside, eucommiol, ajugoside, harpagide and the like Place of harvest: Sichuan, Shaanxi, Hubei, Henan, Guizhou, Yunnan Nature (xìng or qì) and taste: Sweet/slightly acrid, warm. Qì enters the liver/kidney meridans.

Efficacy: Hokanjin (補肝腎, bǔ gān shèn; to tonify liver and kidney), Sokinkotsu (壯筋骨, zhuàng jīn gǔ; to fortify muscle and bone), Antai (安胎, ān tāi; miscarriage prevention), lowering blood pressure Clinical applications: Treatment for Yoshitsu Santsu (腰膝酸痛, yāo xī suān tòng; pain of waist and knee), Kinkotsu Ijaku (筋骨痿弱, jīn gǔ wěi ruò; limp wilting muscle and bone), In'i (陰痿, yīn wěi; impotence), Nyoi Hinsaku (尿意頻数, niào yì pín shù; frequent urination), Zencho Ryuzan (前兆流産, qián zhào liú chǎn; a warning sign of miscarriage), hypertension.

*Lycium* Fruit

Original plant source: Fruit of *Lycium barbarum* L. or *Lycium chinense* Mill. in the family Solanaceae Ingredients: Betaine, physalien and the like Place of harvest: Ningxia, Gansu, Hebei and the like Nature (xìng or qì) and taste: Sweet, flat (neutral). Qì enters the liver/kidney meridians.

Efficacy: Hojin Ekisei (補腎益精, bǔ shèn yì jīng; to tonify kidney and replenish jīng (essence of life)), Yokan Meimoku (養肝明目, yǎng gān míng mù; to nourish the liver to improve visual acuity)

Clinical applications: Treatment for Kanjin Inkyo (肝腎陰虛, gān shèn yīn xū; deficiency of blood and body fluid in the liver and kidney), Yoshitsu San'nan (腰膝酸軟, yāo xī suān ruǎn; dullness and aching of waist and knee), dizziness, visual loss, Shokatsu Isei (消渴遺精, xiāo kě yí jīng; frequent drinking and urination, and spermatorrhea)

*Cistanche* Herb:

Original plant source: Scale-like pulpy substance of *Cistanche deserticola* Y. C. Ma in the family Orobanchaceae Ingredients: Alkaloids, crystalline neutral material and the like Place of harvest: Inner Mongolia and the like Nature (xìng or qì) and taste: Sweet/salty, warm. Qì enters the kidney/large intestine meridians.

Efficacy: Hojinyo (補腎陽, bǔ shèn yáng; to tonify the function of the kidney), Ekisei ketsu (益精血, yì jīng xuè; to boost essence blood), Juncho tsuben (潤腸通便, rùn cháng tōng biàn; to moisten intestine and stimulate bowel movements to excrete waste products)

Clinical applications: Treatment for In'i, Sosetsu (早泄, zǎo xiè; premature ejaculation), Isei (遺精, yí jīng; spermatorrhea), Fuyo (不孕, bú yùn; infertility), enuresis, Yoshitsu San'nan, Kinkotsu Ijaku, Kekko Benpi (血枯 便秘, xuè kū biàn mì; constipation due to exhaustion of blood).

*Dioscorea* Rhizome

Original plant source: Rhizome of *Dioscorea batatas* Decne. in the family Dioscoteaceae Ingredients: Dopamine, abscisin II, choline, tannin and a variety of amino acids and the like Place of harvest: Henan, Shanxi, Hebei, Shaanxi and the like Nature (xìng or qì) and taste: Sweet, flat (neutral). Qì enters the spleen/lung/kidney meridians.

Efficacy: Kenpi I (健脾胃, jiàn pí wèi; to tonify spleen and stomach), Ekihaijin (益肺腎, yì fèi shèn; to fortify lung and kidney), Hokyorui (補虛羸, bǔ xū léi; to fortify weak constitution).

Clinical applications: Treatment for Hikyo Sessha (脾虛泄瀉, pí xū xiè xiè; deficiency of the functions of spleen, and severe diarrhea), Haikyo Gaiso (肺虛咳嗽, fèi xū ké sòu; coughing due to deficiency of body liquid in the lung,), Shokatsu (消渴, xiāo kě; frequent drinking and urination), Shoben Hinsaku (小便頻数, xiǎo biàn pín shù; urinary frequency), Isei, Kyoro Ruiso (虛勞羸瘦, xū láo léi shòu; emaciation due to deficiency of the functions of the five internal organs), Shokusho Kentai (食少倦怠, shí shǎo juàn dài; small appetite and fatigue), chronic nephritis, child enuresis, leukorrhea.

*Cornus* Fruit:

Original plant source: Fruits of *Cornus officinalis* Sieb. et Zucc. in the family Cornaceae Ingredients: Morroniside, 7-methyl-morroniside, sweroside, loganin, cornin, ursolic acid, gallic acid, malic acid, tartaric acid, tannin, saponin, and the like Place of harvest: Zhejiang, Henan, Anhui, Shaanxi, Shanxi, Shandong, Sichuan, and the like Nature (xìng or qì) and taste: Sour, lukewarm. Qì enters the liver/kidney meridians.

Efficacy: Hoeki Jinkan (補益腎肝, bǔ yì shèn gān; to tonify kidney and liver), Jusei Renkan (澀精斂汗, sè jīng liǎn hàn; to arrest seminal emission and sweating).

Clinical applications: To'un (頭暈, tóu yūn; dizzy), dizziness, tinnitus, Yoshitsu San'nan, Isei Kassetsu (遺精 滑泄, yí jīng huá xiè; sperrnatorrhea and lingering diarrhea), enuresis, Rojin Nyohin Shikkin (老人尿頻失禁, lǎo rén niào pín shī jìn; senile frequent urination and incontinence), Kyokan Fushi (虛汗不止, xū hàn bù zhǐ; persistent abnormal sweating due to general debility), hypermenorrhea, Roge Fushi (漏下不止, lòu xià bù zhǐ; persistent metrostaxis).

Next, a method for producing the compositions of the invention will be explained.

Specifically, the compositions of the invention are mixtures of extracts from the Kampo crude drugs mentioned above.

Each crude drug is processed to a size suitable for extraction and mixed at a predetermined ratio. Subsequently, the mixture is extracted to obtain the desired extract.

The extract of the Kampo crude drug used in the invention is the one extracted with water.

In the process of the extraction of the crude drug extracts, it is preferable to use a bag to bundle up the mixed crude drugs in one for an efficient extraction process. It is necessary that the bag does not disturb the extraction process, and that it has robust strength so that it is not torn out even if it is squeezed with strong power.

A preferable bag material is, for example, one used as "Medical supply 04, Formed article, General medical device, Medical gauze, Type 1 (100% cotton, 30 cm in width×10 m in length)".

A rectangular bag is made in an appropriate size (e.g., 18 cm in width×25 cm in height) by processing the bag materials mentioned above. In the process of squeezing a crude drug, strong pressure is applied to the bag used for the extraction. Therefore, it is desirable to make the above-mentioned bag material (gauze) in three layers so that the bag is not ripped.

In addition, similar bag material is desirable to prepare a three-layered string in a suitable size (e.g., 1.5 cm in width×60 cm in length), which ties up the mouth (upper part) of the bag.

For the extraction process of the extract, it is preferable to soak the crude drug for 12 hours in water from which a chlorine component was removed beforehand. Next, the mixture is heated and kept in a boiling state until a crude drug ingredient is sufficiently extracted. As for the duration of the boiling state, it is usually 5 to 10 hours, and may be adjusted as appropriate.

The blending ratio of each crude drug extract in the composition of the invention should be appropriately adjusted depending on the quality and the like of available crude drugs. As for essential crude drugs, for example, the weight ratio of each crude drug to be mixed is within the following ranges.

| Name of crude drug | Range of weight ratio |
| --- | --- |
| Ginseng | 1 to 10, preferably 3 to 8 |
| Atractylodes Rhizome | 5 to 20, preferably 8 to 15 |
| Crataegus Fruit | 10 to 40, preferably 15 to 40 |
| Alisma Tuber | 10 to 30, preferably 15 to 30 |
| Cassia Seed | 5 to 20, preferably 8 to 20 |

For a blending ratio of each crude drug extract to be added in the case of the standard-type fatty liver, for example, the weight ratio of each crude drug to be mixed is within the following ranges.

| Name of crude drug | Range of weight ratio |
| --- | --- |
| Poria Sclerotium | 5 to 20, preferably 8 to 20 |
| Rhubarb | 1 to 10, preferably 2 to 5 |
| Citrus Unshiu Peel | 5 to 20, preferably 5 to 15 |
| Bupleurum Root | 1 to 10, preferably 3 to 8 |
| Astragalus Root | 10 to 30, preferably 15 to 30 |

For a blending ratio of each crude drug extract to be added in the case of the cardiovascular disorder type fatty liver, for example, the weight ratio of each crude drug to be mixed is within the following ranges.

| Name of crude drug | Range of weight ratio |
| --- | --- |
| Salvia Miltiorrhiza Root | 10 to 30, preferably 15 to 30 |
| Pueraria Root | 5 to 20, preferably 8 to 20 |
| Polygonum Root | 5 to 20, preferably 8 to 20 |
| Vaccaria Segetalis | 5 to 20, preferably 8 to 20 |
| Cnidium Rhizome | 5 to 20, preferably 8 to 20 |

For a blending ratio of each crude drug extract to be added in the case of the diabetic mellitus type of fatty liver, for example, the weight ratio of each crude drug to be mixed is within the following ranges.

| Name of crude drug | Range of weight ratio |
| --- | --- |
| Eucommia Bark | 10 to 30, preferably 15 to 30 |
| Lycium Fruit | 5 to 20, preferably 8 to 20 |
| Cistanche Herb | 5 to 20, preferably 8 to 20 |
| Dioscorea Rhizome | 10 to 30, preferably 10 to 25 |
| Cornus Fruit | 10 to 30, preferably 10 to 25 |

Additives that are commonly used in pharmaceutical products including Kampo medicines may be added to the composition of the invention in a range (types and quantities) not affecting the treatment of fatty liver.

For example, the additives that may be optionally added include a sweetener to adjust the taste of the composition of the invention. Specifically, natural sweeteners such as honey, brown sugar, sugar beet and the like are included. However, in the case of the diabetes mellitus type of fatty liver, the addition of sugars mentioned above is not permitted.

The blending amount of any additives mentioned above may be acceptable in an amount not affecting the therapeutic effect of fatty liver. For example, it is preferable to be in 5 to 10 parts by weight per 100 parts by weight as the predetermined total amount of crude drug extract mentioned above.

The dosage form of the composition of the invention is not limited in particular as long as it is in a form for oral administration. The dosage form is basically a liquid formulation, and it may be transformed into powder or granules by means such as freeze-drying, or may be in the form of tablets or capsules.

The dosage when the composition of the invention is given orally as a liquid formulation is not limited in particular, and is usually about 200 mL a day. The daily frequency of dose is not limited in particular, and it is desirable to be administered, for example, twice a day, before breakfast and before bedtime, and in both cases administration should be conducted during the fasting state.

In addition, it is preferable to avoid a diet for about 30 minutes after the administration.

The administration period will be continued until the improvement of the fatty liver can be recognized. According to the following study, a significant improvement was seen after an administration for about three months.

EXAMPLES

The invention will be explained more specifically by showing test examples in which the composition of the invention was manufactured and the improvement of the status of the fatty liver was confirmed for the composition actually administered to patients.

For the extraction of crude drug extracts, an "extraction machine HRS-705" made by SHOWATSUSHO Co., Ltd., an Kampo drug extraction machine, which has an overwhelming domestic market share in Japan, was used.

Example A: Preparation of an Extract for Type A (Standard Type)

In the preparation of the extract, the following two extraction processes and one concentration process were conducted using the extraction machine mentioned above.

In the first "crude drug extract extraction process", crude drugs of the composition for type A as shown in the following Table 2 were mixed at a predetermined ratio, and the total of 120 g of crude drug mixtures is placed in a bag (18 cm in width×25 cm in height made with three-layered gauze). After immersing two of the bag (120×2) into 5,000 mL of water for 12 hours, the mixture was charged into the crude drug extraction machine, and the extraction operation time on the thermoswitch was set for 180 minutes (three hours).

When the temperature inside the tank reaches 92° C., the crude drug extraction machine was set so that the thermoswitch indicating the extraction time was automatically turned on and started to operate. In addition, it takes about 80 seconds to raise the temperature inside the tank by 1° C. Since the temperature of the mixed water was 12° C., it took about 106 minutes until the temperature reached 92° C. and the thermoswitch started to operate. The temperature inside the tank rose up to a maximum temperature of 106° C. after the thermoswitch was operated.

Thus, for the extraction time of the first crude drug extract, it took 106 minutes to prepare the operation of the machine, then 180 minutes for extracting the crude drug extract, and a total of 286 minutes (four hours 46 minutes).

At the point when the switch of the crude drug extraction machine was turned OFF, 3,000 mL of the extract liquid was taken out of the tank. At that time, the bag of the mixed crude drugs and extract residual liquid was left in the tank of the extraction machine.

By the first extraction, the amount of vapor released to the outside of the tank was about 1,200 mL.

For the second "extraction of the crude drugs", 3,000 mL of water was newly poured into the tank and the thermoswitch was set at 120 minutes.

Since the temperature in the tank was 55° C. when the second extraction was initiated, it took about 50 minutes to prepare the operation of the machine until the thermoswitch was turned ON, then 120 minutes for extracting the crude drug extract, and a total of 170 minutes (2 hours 50 minutes).

All the extract liquid was taken out of the tank when the thermoswitch mentioned above was turned OFF, then the bag of crude drugs was taken out and squeezed, and the extract liquid squeezed was added to the second extract liquid.

By the second extraction, the amount of vapor released out of the tank was about 800 mL, and the mixed crude drug residue including the moisture after squeezing was about 600 g. Therefore, the extraction amount obtained by the second extraction was about 2,400 mL.

In the concentration process, a total of 5,400 mL of the crude drug extract liquid obtained by the first and second extractions was re-charged into the extraction machine. Subsequently, the thermoswitch was set to 90 minutes, and the extract liquid was concentrated.

Since about 600 mL of vapor was released in the concentration process, about 4,800 mL of crude drug extract liquid was finally obtained.

This crude drug extract liquid was filled in an aluminum pack for each 100 mL. The aluminum pack filled with the crude drug extract was subjected to heat sterilization for 40 minute at 100° C. by steam convection process.

Example B: Preparation of an Extract for Type B (Hypertension Complication Type)

The preparation was conducted in a similar way to Example A except that the crude drugs shown in the following Table 2 were used at the weight indicated in Table 2, respectively, to obtain about 4,800 mL of the extract for Type B.

Example C: Preparation of an Extract for Type C (Diabetes Mellitus Complication Type)

The preparation was conducted in a similar way to Example A except that the crude drugs shown in the following Table 2 were used at the weight indicated in Table 2, respectively, to obtain about 4,700 mL of the extract for Type C.

TABLE 2

| Name of crude drug | Extract for Type A | Extract for Type B | Extract for Type C |
| --- | --- | --- | --- |
| Ginseng | 5 | 5 | 5 |
| Atractylodes Rhizome | 10 | 10 | 10 |
| Cragaegus Fruit | 30 | 20 | 30 |
| Alisma Tuber | 20 | 20 | 20 |
| Cassia Seed | 10 | 10 | 10 |
| Poria Sclerotium | 10 | — | — |
| Rhubarb | 3 | — | — |
| Citrus Unshiu Peel | 7 | — | — |
| Bupleurum Root | 5 | — | — |
| Astragalus Root | 20 | — | — |
| Salvia Miltiorrhiza Root | — | 20 | — |
| Pueraria Root | — | 10 | — |
| Polygonum Root | — | 10 | — |
| Vaccaria Segetalis | — | 10 | — |
| Cnidium Rhizome | — | 10 | — |
| Eucommia Bark | — | — | 20 |
| Lycium Fruit | — | — | 10 |
| Cistanche Herb | — | — | 10 |
| Dioscorea Rhizome | — | — | 15 |
| Cornus Fruit | — | — | 15 |
| Total amount | 120 g | 125 g | 145 g |

Test Example

In the following study, the classification of the type of subjects, laboratory data and clinical findings were provided by Professor Takeshi Kurihara, M. D. at Tokyo Women's Medical University.

Subjects

Fifteen patients who had fatty liver based on diagnosis by abdominal ultrasonography, and the values of either AST (aspartate aminotransferase) or ALT (alanine aminotransferase) exceeding their reference values of 20 IU/L, were selected as subjects. None of them had shown therapeutic effects after dietary therapy and exercise therapy.

Fifteen patients were classified into the following three types in consideration of the five kinds of classification based on Clinical Chinese Traditional Medicine and from the viewpoint of Western medicine.

Type A: Patients who shows only fatty liver (3 cases)

Type B: Patients complicated by hypertension (7 cases) (patients who are administered an antihypertensive agent, and show 140 mmHg or more of systolic blood pressure or 90 mmHg or more of diastolic blood pressure (based on the guideline of the Japanese Society of Hypertension 2004 version))

Type C: Patients complicated by diabetes mellitus (7 cases) (patients who show 126 mg/dL or more of fasting blood glucose levels or 200 mg/dL or more of casual blood glucose levels (based on the guideline of the Japan Diabetes Society 2006 through 2007))

Administration Method

An extract for each type produced in Examples A to C mentioned above was orally administered twice daily (morning and evening) for three months. In addition, in case where the administration twice daily was impossible, the drink was administered once daily instead.

The administration period was set for three months from the beginning of dosage.

During the administration period, subjects were not given any special dietary instructions, alcohol drinking regulation nor exercise therapy, but left on a voluntary basis.

Follow-Up

Before starting the test and every month during the test, a hematological examination was carried out over time, and significant difference was tested with a statistical analysis.

Results from the analysis was shown in the following Table 3 for Type A subjects of, the following Table 4-1 and 4-2 for Type B subjects, and the following Tables 5-1 and 5-2 for Type C subjects.

TABLE 3

| | Subjects | | | | | | | | | | | |
|---|---|---|---|---|---|---|---|---|---|---|---|---|
| | S.M | | | | I.W | | | | M.H | | | |
| | Gender | | | | | | | | | | | |
| | M | | | | F | | | | M | | | |
| | Age | | | | | | | | | | | |
| | 69 | | | | 24 | | | | 60 | | | |
| | Examination date | | | | | | | | | | | |
| | Pre | After 1 m. | After 2 m. | After 3 m. | Pre | After 1 m. | After 2 m. | After 3 m. | Pre | After 1 m. | After 2 m. | After 3 m. |
| Body weight | 63 | 62.2 | 60.3 | 59.9 | 90.3 | 87.5 | 87.1 | 87.3 | 62.4 | 61.8 | 61.3 | 60.5 |
| Systolic blood pressure | 122 | 118 | 122 | 120 | 122 | 116 | 120 | 122 | 128 | 120 | 134 | 126 |
| Diastolic blood | 76 | 72 | 70 | 78 | 72 | 70 | 70 | 70 | 78 | 82 | 80 | 76 |
| Total protein | 7.8 | 7.8 | 7.7 | 7.8 | 7.7 | 8.2 | 8 | 7.9 | 7.6 | 7.9 | 7.7 | 7.9 |
| Albumin | 4.5 | 4.6 | 4.4 | 4.6 | 4.5 | 4.7 | 4.7 | 4.7 | 4.4 | 4.5 | 4.5 | 4.6 |
| AST | 39 | 38 | 34 | 29 | 50 | 43 | 40 | 39 | 52 | 29 | 38 | 30 |
| ALT | 67 | 64 | 48 | 40 | 117 | 91 | 88 | 82 | 46 | 28 | 34 | 27 |
| γGTP | 115 | 127 | 122 | 108 | 66 | 56 | 54 | 49 | 223 | 220 | 289 | 337 |
| Blood glucose | 100 | 99 | 101 | 93 | 87 | 77 | 86 | 73 | 106 | 105 | 102 | 101 |
| HbAlc | 5.6 | 5.5 | 5.5 | 5.7 | 4.9 | 5 | 4.5 | 4.5 | 5 | 5 | 4.9 | 5.1 |
| T-Cho | 157 | 160 | 156 | 153 | 172 | 152 | 144 | 157 | 193 | 212 | 207 | 189 |
| HDL-C | 32 | 34 | 33 | 32 | 62 | 51 | 53 | 63 | 54 | 56 | 52 | 50 |
| LDL-C | 111 | 117 | 115 | 109 | 108 | 100 | 94 | 103 | 66 | 87 | 78 | 70 |
| TG | 189 | 156 | 191 | 177 | 95 | 157 | 63 | 90 | 441 | 500 | 478 | 398 |
| Adiponectin | 9.1 | — | — | 11.6 | 3.7 | — | — | 6.5 | 3.7 | — | — | 5.8 |
| CT visceral | 107.7 | — | — | — | 95.6 | — | — | — | — | — | — | — |
| subcutaneous | 110.8 | — | — | — | 100.8 | — | — | — | — | — | — | — |
| Waist | 82.4 | — | — | — | 79.4 | — | — | — | — | — | — | — |
| Findings | Diarrhea symptoms started at week 2 after initiaing the test, discontinued medication temporary at week 3, later started the administration once a day at week 5. No symptoms of diarrhea was recognized. The improvement of liver functions and the body weight loss and reduction of visceral fat were also confirmed in CT. | | | | The improvement of liver functions was remarkable compared to the body weight loss. | | | | The body weight decreased, and liver functions tended to improve. | | | |

TABLE 4-1

| | Subjects | | | | | | | | | | | |
|---|---|---|---|---|---|---|---|---|---|---|---|---|
| | F.K | | | | O.T | | | | A.H | | | |
| | Gender | | | | | | | | | | | |
| | M | | | | M | | | | F | | | |
| | Age | | | | | | | | | | | |
| | 39 | | | | 55 | | | | 62 | | | |
| | Examination date | | | | | | | | | | | |
| | Pre | After 1 m. | After 2 m. | After 3 m. | Pre | After 1 m. | After 2 m. | After 3 m. | Pre | After 1 m. | After 2 m. | After 3 m. |
| Body weight | 103.8 | 104.4 | 103.7 | 104.9 | 84.5 | 81.4 | 81.3 | 80.5 | 83.8 | 83.9 | 84.2 | 84.8 |
| Systolic blood | 152 | 150 | 136 | 142 | 135 | 118 | 114 | 124 | 168 | 146 | 142 | 142 |
| Diastolic blood | 100 | 100 | 100 | 96 | 100 | 82 | 80 | 84 | 100 | 94 | 90 | 90 |
| Total protein | 7.9 | 8.2 | 7.9 | 8 | 6.9 | 7.1 | 7.2 | 7.1 | 7.9 | 8 | 7.9 | 8.1 |
| Albumin | 4.9 | 5.1 | 4.8 | 5 | 4.4 | 4.6 | 4.7 | 4.6 | 4.9 | 5.1 | 5 | 5.1 |
| AST | 42 | 34 | 37 | 31 | 39 | 21 | 19 | 21 | 38 | 32 | 22 | 24 |
| ALT | 87 | 80 | 77 | 69 | 48 | 23 | 25 | 19 | 46 | 33 | 25 | 26 |
| γGTP | 68 | 61 | 68 | 63 | 107 | 64 | 67 | 67 | 53 | 47 | 43 | 45 |
| Blood glucose | 125 | 138 | 169 | 186 | 107 | 100 | 128 | 100 | 110 | 75 | 93 | 98 |
| HbAlc | 6.7 | 6.5 | 6.8 | 6.9 | 5.4 | 5.4 | 4.8 | 5.4 | 5.4 | 5.5 | 5.7 | 5.7 |
| T-Cho | 285 | 244 | 250 | 233 | 165 | 190 | 168 | 233 | 233 | 246 | 234 | 243 |
| HDL-C | 61 | 53 | 62 | 59 | 51 | 45 | 49 | 44 | 52 | 52 | 60 | 57 |
| LDL-C | 190 | 167 | 161 | 158 | 99 | 119 | 108 | 152 | 162 | 160 | 165 | 178 |
| TG | 267 | 234 | 212 | 154 | 241 | 166 | 69 | 267 | 261 | 294 | 179 | 202 |
| Adiponectin | 5.7 | — | — | 6.9 | 7.8 | — | — | 11.7 | 4.8 | — | — | 7.1 |

TABLE 4-1-continued

| | Subjects | | | | | | | | | | | |
|---|---|---|---|---|---|---|---|---|---|---|---|---|
| | F.K | | | | O.T | | | | A.H | | | |
| | Gender | | | | | | | | | | | |
| | M | | | | M | | | | F | | | |
| | Age | | | | | | | | | | | |
| | 39 | | | | 55 | | | | 62 | | | |
| | Examination date | | | | | | | | | | | |
| | Pre | After 1 m. | After 2 m. | After 3 m. | Pre | After 1 m. | After 2 m. | After 3 m. | Pre | After 1 m. | After 2 m. | After 3 m. |
| CT visceral | 248.8 | — | — | — | — | — | — | — | — | — | — | — |
| subcutaneous | 298.5 | — | — | — | — | — | — | — | — | — | — | — |
| Waist | 111.7 | — | — | — | — | — | — | — | — | — | — | — |
| Findings | The liver functions showed a tendency to improve although the body weight tended to increase and the blood glucose level increased due to overeating, The blood pressure also tended to decline. | | | | The body weight decreased sharply. In the second half of medication, triglyceride and cholesterol increased due to overeating tendency, but ALT declined. The blood pressure also declined. | | | | The liver functions improved, although the body weight tended to increase and HbA1c also aggravated. The blood pressure also tended to decrease. | | | |

TABLE 4-2

| | Subjects | | | | | | | | | | | |
|---|---|---|---|---|---|---|---|---|---|---|---|---|
| | Y.M | | | | A.N | | | | S.T | | | |
| | Gender | | | | | | | | | | | |
| | M | | | | M | | | | M | | | |
| | Age | | | | | | | | | | | |
| | 67 | | | | 55 | | | | 66 | | | |
| | Examination date | | | | | | | | | | | |
| | Pre | After 1 m. | After 2 m. | After 3 m. | Pre | After 1 m. | After 2 m. | After 3 m. | Pre | After 1 m. | After 2 m. | After 3 m. |
| Body weight | 74.8 | 74.1 | 73.9 | 74.7 | 97.4 | 97.7 | 98.2 | 97.6 | 74 | 74.6 | 74.1 | 73.7 |
| Systolic blood | 178 | 146 | 142 | 146 | 158 | 134 | 124 | 126 | 146 | 132 | 130 | 138 |
| Diastolic blood | 108 | 94 | 86 | 84 | 96 | 84 | 82 | 86 | 88 | 84 | 82 | 84 |
| Total protein | 8.2 | 8.3 | 8.3 | 8.3 | 7.7 | 8 | 7.6 | 7.7 | 6.9 | 6.9 | 7.1 | 6.6 |
| Albumin | 4.4 | 4.4 | 4.3 | 4.4 | 4.4 | 4.4 | 4.4 | 4.4 | 4.4 | 4.4 | 4.4 | 4.2 |
| AST | 70 | 65 | 60 | 56 | 46 | 28 | 23 | 26 | 48 | 39 | 43 | 43 |
| ALT | 46 | 35 | 32 | 32 | 55 | 51 | 37 | 44 | 47 | 32 | 41 | 37 |
| γGTP | 288 | 249 | 207 | 203 | 86 | 83 | 78 | 90 | 255 | 281 | 288 | 243 |
| Blood glucose | 103 | 103 | 105 | 99 | 102 | 112 | 106 | 102 | 125 | 115 | 112 | 97 |
| HbA1c | 5.9 | 5.6 | 6 | 5.9 | 5.6 | 5.5 | 5.5 | 5.5 | 4.8 | 4.7 | 4.7 | 4.7 |
| T-Cho | 271 | 261 | 303 | 256 | 204 | 206 | 213 | 208 | 156 | 158 | 168 | 149 |
| HDL-C | 115 | 103 | 124 | 98 | 43 | 43 | 45 | 42 | 40 | 45 | 38 | 42 |
| LDL-C | 140 | 143 | 153 | 134 | 133 | 120 | 120 | 117 | 67 | 66 | 66 | 59 |
| TG | 84 | 119 | 91 | 75 | 339 | 204 | 246 | 311 | 416 | 335 | 535 | 394 |
| Adiponectin | 10.4 | — | — | 12.3 | 2.2 | — | — | 3.2 | 5.9 | — | — | 6.6 |
| CT visceral | — | — | — | — | — | — | — | — | — | — | — | — |
| subcutaneous | — | — | — | — | — | — | — | — | — | — | — | — |
| Waist | — | — | — | — | — | — | — | — | — | — | — | — |
| Findings | Although the body weight was unchanged, and the lipid level fluctuated, the function of the liver tended to improve mildly. The blood pressure was improved. | | | | Increase or decrease in the body weight was not observed, but the function of the liver tended to improve. In the second half of the medication, the amount of alcohol drinking increased, and γGTP, TG levels were elevated. However, the blood pressure decreased. | | | | Increase or decrease in the body weight was not observed, and the laboratory data was slightly improved, but it was almost invariable. | | | |

TABLE 5-1

| | Subjects | | | | | | | | | | | |
|---|---|---|---|---|---|---|---|---|---|---|---|---|
| | S.M | | | | N.F | | | | W.T | | | |
| | Gender | | | | | | | | | | | |
| | M | | | | F | | | | M | | | |
| | Age | | | | | | | | | | | |
| | 61 | | | | 39 | | | | 48 | | | |
| | Examination date | | | | | | | | | | | |
| | Pre | After 1 m. | After 2 m. | After 3 m. | Pre | After 1 m. | After 2 m. | After 3 m. | Pre | After 1 m. | After 2 m. | After 3 m. |
| Body weight | 65.1 | 64.5 | 64.1 | 63.2 | 78.9 | 80.6 | 81.3 | 81 | 123.1 | 122.9 | 121.7 | 119.8 |
| Systolic blood pressure | 130 | 120 | 124 | 128 | 124 | 118 | 118 | 128 | 136 | 132 | 140 | 136 |
| Diastolic blood pressure | 80 | 80 | 82 | 84 | 92 | 90 | 82 | 86 | 98 | 92 | 88 | 94 |
| Total protein | 7.2 | 7.6 | 7 | 7.3 | 7.8 | 8.1 | 7.8 | 7.9 | 7.4 | 7.3 | 7.4 | 7 |
| Albumin | 4.7 | 5.1 | 4.6 | 4.6 | 4.5 | 4.7 | 4.6 | 4.6 | 4.7 | 4.6 | 4.7 | 4.3 |
| AST | 21 | 19 | 13 | 15 | 112 | 78 | 68 | 72 | 86 | 49 | 48 | 42 |
| ALT | 19 | 11 | 8 | 11 | 147 | 129 | 112 | 119 | 82 | 53 | 50 | 47 |
| γGTP | 81 | 70 | 64 | 68 | 76 | 70 | 63 | 68 | 152 | 141 | 139 | 129 |
| Blood glucose | 195 | 107 | 182 | 222 | 181 | 141 | 149 | 158 | 139 | 130 | 132 | 140 |
| HbA1c | 8.9 | 8.6 | 8.9 | 9.3 | 6.4 | 6.2 | 6.3 | 6.1 | 7 | 6.9 | 6.8 | 6.6 |
| T-Cho | 165 | 178 | 135 | 163 | 250 | 313 | 248 | 239 | 221 | 204 | 219 | 200 |
| HDL-C | 95 | 57 | 64 | 62 | 65 | 59 | 65 | 62 | 72 | 60 | 71 | 70 |
| LDL-C | 93 | 98 | 69 | 97 | 163 | 200 | 174 | 181 | 150 | 127 | 142 | 118 |
| TG | 95 | 158 | 119 | 72 | 174 | 279 | 175 | 193 | 214 | 226 | 209 | 254 |
| Adiponectin | 2.6 | — | — | 3.9 | 3.9 | — | — | 5.3 | 2.9 | — | — | 5.1 |
| Leptin | — | — | — | — | — | — | — | — | — | — | — | — |
| CT visceral | 100.1 | — | — | 95.8 | — | — | — | — | — | — | — | — |
| subcutaneous | 91.3 | — | — | 93.5 | — | — | — | — | — | — | — | — |
| Waist | 81.3 | — | — | 80.1 | — | — | — | — | — | — | — | — |
| Findings | The liver functions showed an improving tendency. CT showed a decrease of visceral fat. | | | | Despite the body weight gain, the liver functions and the blood glucose level were improved. | | | | Both the liver functions and the blood glucose level improved along with the body weight loss. | | | |

TABLE 5-2

| | Subjects | | | | | | | | | | | |
|---|---|---|---|---|---|---|---|---|---|---|---|---|
| | S.M | | | | N.F | | | | W.T | | | |
| | Gender | | | | | | | | | | | |
| | M | | | | F | | | | M | | | |
| | Age | | | | | | | | | | | |
| | 61 | | | | 39 | | | | 48 | | | |
| | Examination date | | | | | | | | | | | |
| | Pre | After 1 m. | After 2 m. | After 3 m. | Pre | After 1 m. | After 2 m. | After 3 m. | Pre | After 1 m. | After 2 m. | After 3 m. |
| Body weight | 65.1 | 64.5 | 64.1 | 63.2 | 78.9 | 80.6 | 81.3 | 81 | 123.1 | 122.9 | 121.7 | 119.8 |
| Systolic blood pressure | 130 | 120 | 124 | 128 | 124 | 118 | 118 | 128 | 136 | 132 | 140 | 136 |
| Diastolic blood pressure | 80 | 80 | 82 | 84 | 92 | 90 | 82 | 86 | 98 | 92 | 88 | 94 |
| Total protein | 7.2 | 7.6 | 7 | 7.3 | 7.8 | 8.1 | 7.8 | 7.9 | 7.4 | 7.3 | 7.4 | 7 |
| Albumin | 4.7 | 5.1 | 4.6 | 4.6 | 4.5 | 4.7 | 4.6 | 4.6 | 4.7 | 4.6 | 4.7 | 4.3 |
| AST | 21 | 19 | 13 | 15 | 112 | 78 | 68 | 72 | 86 | 49 | 48 | 42 |
| ALT | 19 | 11 | 8 | 11 | 147 | 129 | 112 | 119 | 82 | 53 | 50 | 47 |
| γGTP | 81 | 70 | 64 | 68 | 76 | 70 | 63 | 68 | 152 | 141 | 139 | 129 |
| Blood glucose | 195 | 107 | 182 | 222 | 181 | 141 | 149 | 158 | 139 | 130 | 132 | 140 |
| HbA1c | 8.9 | 8.6 | 8.9 | 9.3 | 6.4 | 6.2 | 6.3 | 6.1 | 7 | 6.9 | 6.8 | 6.6 |
| T-Cho | 165 | 178 | 135 | 163 | 250 | 313 | 248 | 239 | 221 | 204 | 219 | 200 |
| HDL-C | 95 | 57 | 64 | 62 | 65 | 59 | 65 | 62 | 72 | 60 | 71 | 70 |
| LDL-C | 93 | 98 | 69 | 97 | 163 | 200 | 174 | 181 | 150 | 127 | 142 | 118 |
| TG | 95 | 158 | 119 | 72 | 174 | 279 | 175 | 193 | 214 | 226 | 209 | 254 |
| Adiponectin | 2.6 | — | — | 3.9 | 3.9 | — | — | 5.3 | 2.9 | — | — | 5.1 |
| Leptin | — | — | — | — | — | — | — | — | — | — | — | — |
| CT visceral | 100.1 | — | — | 95.8 | — | — | — | — | — | — | — | — |
| subcutaneous | 91.3 | — | — | 93.5 | — | — | — | — | — | — | — | — |
| Waist | 81.3 | — | — | 80.1 | — | — | — | — | — | — | — | — |
| Findings | The liver functions showed an improving tendency. CT showed a decrease of visceral fat. | | | | Despite the body weight gain, the liver functions and the blood glucose level were improved. | | | | Both the liver functions and the blood glucose level improved along with the body weight loss. | | | |

For the examination items in the Tables mentioned above were determined using the conventional laboratory procedure that has been clinically used. The units of each measurement value are described in the parentheses.

Total protein: total protein amount (g/dL) in the blood
Albumin: albumin amount (g/dL) in the blood
AST: aspartate aminotransferase (U/L)
ALT: alanine aminotransferase (U/L)
γGTP: γ-glutamyl transpeptidase (U/L)
HbA1c: glycohemoglobin A1c (%)
T-Cho: total cholesterol (mg/dL)
HDL-C: high-density cholesterol (mg/dL)
LDL-C: low-density cholesterol (mg/dL)
TG: triglyceride (mg/dL)
CT visceral: area of visceral fat ($cm^2$) measured by using computed tomography (CT)
Subcutaneous: area of subcutaneous fat ($cm^2$) measured by using computed tomography (CT)
Waist: waist circumference (cm)

Discussions

In all the subjects, the AST level (P=0.011) and the maximum blood pressure (P=0.025) were significantly decreased three months after the administration of the extract compared to the levels before the administration.

In addition, a tendency to decrease was found in the ALT level (P=0.066), and the adiponectin level (0.063) showed a tendency to increase.

Any particular changes in the measured values except the above results were not recognized, and no value became exacerbated.

In two subjects, the area of the visceral fat in the umbilical part was measured by CT. Subsequent observation of their outcome revealed that the area of the visceral fat decreased in both cases.

It was thought that the decrease of AST and ALT was a result of the decline of the extent of fatty deposition in the liver. In addition, the presentation of a rising trend in the adiponectin level, a marker of metabolic syndrome, indicates a decrease in visceral fat. In other words, it is expected that adiponectin, beneficial adipocytokine, produced in visceral fat cells increases, and the activation of glycometabolism and the suppression of obesity occur.

Obesity was examined by measuring the body weight, but no change in the body weight was observed. Even though no changes in the body weight were observed, the decline of fat deposits in the liver demonstrates most clearly that the extract used in the invention is useful for treating fatty liver.

When each case was individually examined (referred as Tables), in many subjects, the body weight, or HbA1c, TG (triglyceride) was elevated, however, the decrease of AST and ALT was recognized.

In addition, although the test was carried out under severe conditions in which all the restrictions such as diet, alcohol drinking, exercise therapy, and the like by the subjects were on a voluntary basis, the improvement effect on fatty liver or liver functions was recognized. Through such an objective fact, it can be said that the composition of the invention has an extremely advantageous effect compared to medicines currently prescribed.

INDUSTRIAL APPLICABILITY

The composition of the invention (extract) is very useful for the treatment of fatty liver.

The composition of the invention (extract) is very useful for the treatment of fatty liver that is not improved by dietary therapy, exercise therapy, medical treatment by Western medicine.

The composition of the invention (extract) is expected to show a tremendous therapeutic effect if it is used in conjunction with diet therapy and/or exercise therapy.

Some embodiments and/or Examples of the invention were explained in details above. For those skilled in the art, it is easy to add many modifications to the embodiments and/or Examples, which are only for exemplification, substantially not apart from the new teach and effects of the invention. Therefore, these many modifications are included within the scope of the invention.

The entire content of the references cited in the description and the description of the Japanese Patent Application that serves as the basis for the right of priority provided for in the Paris Convention is incorporated herein by reference.

The invention claimed is:

1. A therapeutic composition for treating fatty liver, comprising an extract of *Ginseng, Atractylodes* Rhizome, *Crataegus* Fruit, *Alisma* Tuber, *Cassia* Seed, *Poria Sclerotium*, Rhubarb, *Citrus Unshiu* Peel, *Bupleurum* Root and *Astragalus* Root, wherein the extract is prepared by:

processing each crude *Ginseng, Atractylodes* Rhizome, *Crataegus* Fruit, *Alisma* Tuber, *Cassia* Seed, *Poria Sclerotium*, Rhubarb, *Citrus Unshiu* Peel, *Bupleurum* Root and *Astragalus* Root to a size suitable for extraction;

mixing processed crude *Ginseng, Atractylodes* Rhizome, *Crataegus* Fruit, *Alisma*, Tuber, *Cassia* Seed, *Poria Sclerotium*, Rhubarb, *Citrus Unshiu* Peel, *Bupleurum* Root and *Astragalus* Root at a predetermined ratio, thereby obtaining a mixture;

soaking the mixture in water; and heating the soaked mixture and keeping at a boiling temperature for 5 to 10 hours, thereby obtaining the extract.

2. The therapeutic composition for treating fatty liver according to claim 1, wherein the composition treats fatty liver unaccompanied by a disease other than fatty liver.

3. The therapeutic composition according to claim 1, wherein the therapeutic composition increases adiponectin level in blood.

4. The therapeutic composition according to claim 1, wherein the therapeutic composition reduces transaminase level in blood.

5. The therapeutic composition according to claim 1, wherein the mixture comprises from 1 to 10 wt. % of *Ginseng*, from 5 to 20 wt. % of *Atractylodes* Rhizome, from 10 to 40 wt. % of *Crataegus* Fruit, from 10-30 wt. % of *Alisma* Tuber, from 5 to 20 wt. % of *Cassia* Seed, from 5 to 20 wt. % of *Poria Sclerotium*, from 1 to 10 wt. % of Rhubarb, from 5 to 20 wt. % of *Citrus Unshiu* Peel, from 1 to 10 wt. % of *Bupleurum* Root, and from 10 to 30 wt. % of *Astragalus* Root.

\* \* \* \* \*